United States Patent [19]

Ippolito et al.

[11] Patent Number: 4,681,944

[45] Date of Patent: Jul. 21, 1987

[54] PROCESS FOR PREPARING CERTAIN 1-LOWER ALKANOYL OR BENZOYL-4-(LOWER ALKANOYL OR BENZOYL-METHYLIDENE)-1,4-DIHYDROPYRIDINES OR ACID ADDITION SALTS THEREOF

[76] Inventors: Robert M. Ippolito, 7471 Yonge St., Apt. 707, Thornhill, Ontario, Canada, L3T 2C1; Stephen Vigmond, 291 Avenue Rd., #701, Toronto, Ontario, Canada, M4V 2G9

[21] Appl. No.: 743,499

[22] Filed: Jun. 11, 1985

[51] Int. Cl.[4] .......................................... C07D 211/82
[52] U.S. Cl. ................................ 546/340; 546/314
[58] Field of Search .......................... 546/340, 314

[56] References Cited

U.S. PATENT DOCUMENTS

| | | | |
|---|---|---|---|
| 4,347,363 | 8/1982 | Singh | 546/249 |
| 4,413,127 | 11/1983 | Singh | 546/249 |
| 4,417,054 | 11/1983 | Gelotte | 546/249 |
| 4,469,871 | 9/1984 | Gelotte | 546/249 |

OTHER PUBLICATIONS

Anders et al., Chemische Berichte, vol. 116(9), pp. 3192–3201, Sep. 1983.
March, Advanced Organic Chemistry, Reactions, Mechanisms and Structure, Second Edition, p. 441, McGraw-Hill Pub. QD 251 M2 1977 C.5.
Gutsche and Voges, "Acylation and Other Reactions of 2- and 4-Pyridinylacetonitriles", Sep. 1967, pp. 2685–2689.

*Primary Examiner*—Alan L. Rotman
*Attorney, Agent, or Firm*—Roylance, Abrams, Berdo & Goodman

[57] ABSTRACT

There is described a novel process for preparing 4-pyridinylmethyl ketones of formula (I)

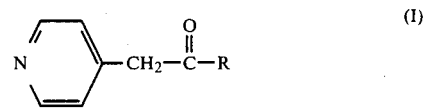

wherein R is alkyl, aryl or aralkyl. The process involves hydrolysis of a compound

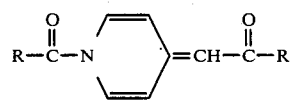

generated by reaction of an acylating agent with 4-methylpyridine. The acylating agent may be selected from compounds of formula R-CO-X and R-CO-O-CO-R where R is as defined above and X represents halogen. Compounds of formula I have utility in the preparation of a variety of products, including pharmaceutically active 1,2-dihydro-6-R-2-oxo-5 pyridinyl compounds.

7 Claims, No Drawings

PROCESS FOR PREPARING CERTAIN 1-LOWER ALKANOYL OR BENZOYL-4-(LOWER ALKANOYL OR BENZOYL-METHYLIDENE)-1,4-DIHYDROPYRIDINES OR ACID ADDITION SALTS THEREOF

BACKGROUND OF THE INVENTION (a) Field of the Invention

This invention relates to a process for preparing (4-pyridinylmethyl) lower alkyl ketones and (4-pyridinylmethyl) aryl ketones and to intermediates useful in such process.

Generally, compounds of the type described herein are useful as intermediates in the preparation of pharmaceutically active 1,2-dihydro-6-R-2-oxo-5-pyridinyl compounds having cardiotonic activity and related such compounds.

(b) Description of the Prior Art

The 4-pyridinylmethyl lower alkyl ketones are generally known compounds which are prepared by known methods; i.e. Rec. Trav. Chim. 72,522 (1953); U.S. Pat. No. 3,133,077 (May 12, 1964), Bull Soc Chim 1968, 4132; Chem Abs 79,8539h (1973); Chem Abstrs. 81, 120 401a (1974); J. Org. Chem 39, 3834 (1974); Chem Abstrs. 87, 6594q, (1977); J. Org Chem 43, 2286 (1978), J Org Chem 22, 939 (1957); U.S. Pat. No. 4,312,875 (Jan. 26, 1982).

All of the preceeding methods describe the synthesis of 2- and 4-pyridinylmethyl alkyl ketones and/or 2- and 4-pyridinylmethyl aryl ketones through acylation of 2-, or 4-pyridinylmethyl anions. A large variety of bases, solvents and acyl equivalents have been used. Few of the methods give high yields and most involve air and moisture sensitive, flammable bases in flammable and expensive etheral solvents and often require exhaustive isolation procedures.

SUMMARY OF THE INVENTION

According to one aspect of the present invention, there is provided a process for preparing a compound of formula I;

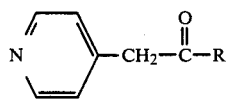
(I)

which comprises hydrolyzing, with alcohol or water, a compound of formula (II)

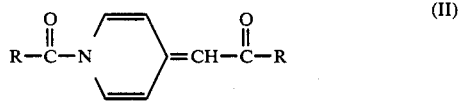
(II)

where R is selected from straight- or branched-chain alkyl, aryl and aralkyl where alkyl is $C_1$-$C_5$.

The intermediate of formula (II) as defined above and salts thereof form a second aspect of the present invention.

According to a third aspect of the invention there is provided a process for preparing the intermediate of formula (II) which comprises reacting 4-methylpyridine with a compound selected from an acyl halide of formula

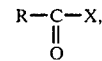

an anhydride of formula

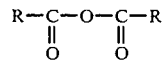

and mixtures thereof where R is as defined above and X represents halogen, preferably chlorine or bromine. Particularly preferred embodiments of the invention are those in which R is selected from methyl, ethyl and phenyl. The intermediate of formula II may be reacted either after isolation or in situ to provide the ketone of formula I as described.

Generally, the process aspect of the present invention provides a method for preparing (4-pyridinylmethyl) ketones which has the advantage of simplicity with attendant good yields. The starting materials used in preparing the intermediate of formula II are relatively cheap and abundant, making the overall process cost attractive. Moreover, exhaustive isolation steps are not generally required.

DETAILED DESCRIPTION OF THE PREFERRED EMBODIMENTS

The overall process of the invention is conducted by first combining the selected acyl halide, anhydride or mixture thereof with 4-methylpyridine in suitable solvents. Preferred solvents include dichloromethane, chloroform and other chlorinated solvents, best results having been obtained with solvents capable of maintaining the intermediate, generated during the reaction, in solution.

The reaction may be performed with a molar ratio of acylating agent: 4-methylpyridine from 5:1 to 1:1, most preferably about 1.5-2.5:1.

In cases where an anhydride is to serve as acylating agent, an additional mole of anhydride may serve as solvent. Also, to conduct the reaction with anhydride, a catalytic amount of acyl halide or strong anhydrous acids including mineral acids selected from HCl, HBr, HI and $H_2SO_4$ and including organic acids selected from p-toluenesulfonic acid, methane toluenesulfonic acid and trifluoroacetic acid may be added to the reaction vessel to obtain best results.

The initial combination of acylating agent and 4-methylpyridine will generate an exothermic reaction, the temperature of which is preferably maintained at or below room temperature. Where acyl halide is employed, initial temperatures suitably range from 0°-20° C., preferably 10° C. and where anhydride is used, room temperature is more suitable. Thereafter, the temperature may be raised, eg. up to 80° C., to drive the reaction to completion preferably with attendant agitation of the mixture.

Upon completion, the intermediate of formula II may be isolated from the vessel in free base form, preferably, or in acid addition salt form, depending on the isolation technique employed, details of which will be apparent to those skilled in the art.

To provide the ketone of formula I, the intermediate and/or its acid addition salt is hydrolyzed, either in situ or after isolation, with alcohol or water. Suitable alcohols are the lower alkanols i.e. $C_1$, -$C_5$ with methanol, ethanol and isopropanol being preferred. Thereafter, the ketone of formula I is isolated by standard, known techniques. p In the alternative, the step of isolation of the intermediate of formula II from this product mixture may be omitted, and the hydrolysis reaction with water or alcohol conducted on the product mixture itself. Theoretically, it is possible that not all of the reaction product which is to be hydrolyzed is in the form of intermediate II or its acid addition salts, due to further reaction of the intermediate with other products in the reaction mixture. Accordingly, it will be understood that the in situ reaction need not necessarily progress exclusively through hydrolysis of intermediate II or its acid addition salts. In such conditions, the hydrolysis step of the reaction is more appropriately defined as being effected on the reaction products of the acylating agent, 4-methylpyridine and catalyst.

The invention is further illustrated in the following non-limiting examples:

EXAMPLE 1

1-acetyl-4-(acetylmethylidene)-1,4-dihydropyridine

To 50 g 4-methylpyridine in 200 ml dichloromethane maintained at 10° C. was added dropwise over 1-2 hours a solution of 84.4 g acetyl chloride in 100 ml dichloromethane. Upon completion of the addition the temperature was allowed to rise to room temperature and stirring was continued for 8-16 hours. The red solution was quenched into saturated sodium carbonate solution and the organic layer separated. On removal of the dichloromethane under reduced pressure, toluene was added and ½ to ⅓ of the 4-methylpyridine was removed by azeotropic distillation under reduced pressure. The residue of 4-methylpyridine and desired product was then cooled in ice. After filtration and washing with cold toluene 24 g of 1-acetyl-4-(acetylmethylidene)-1,4-dihydropyridine was obtained as a bright yellow solid; m.p. 152°-154° C. Additional crops of desired material can be recovered from the filtrate by removal of additional 4-methylpyridine and cooling.

EXAMPLE 2

1-(4-pyridinyl)-2-propanone.

To 20 g of 1-acetyl-4(acetylmethylidene)-1,4-dihydropyridine was added 30 ml ethanol and the mixture refluxed 4 to 8 hours. Upon removal of solvent, 15 g of 1-(4-pyridinyl)-2-propanone was obtained as a light yellow oil.

EXAMPLE 3

1-(4-pyridinyl)-2-propanone

To 10 g of 4-methylpyridine and 32.75 g acetic anhydride, maintained at room temperature, was added 1 ml of acetyl chloride, dropwise over 5-10 min. The solution was then warmed to 50° C. for 6-16 hours. The black reaction mixture was then cooled to 0° C. and 100 mls of ethanol, was added dropwise. The reaction mixture was stirred for 1 hour after the addition, then refluxed for 4-12 hours. The alcohol was removed under reduced pressure and the residue taken up in 100-150 ml methylene chloride. The methylene chloride was washed 2 times with saturated 50 ml portions of sodium carbonate solution then dried over sodium sulfate and evaporated under reduced pressure. Toluene was added to the residue and the excess 4-methylpyridine removed by azeotropic distillation under reduced pressure. Yield: 4.3 gm of 4-pyridinyl-2-propanone.

Use of anhydrous $H_2SO_4$ as catalyst in place of acetyl chloride, entails a similar procedure to that described above. However, only about 5 drops of such acid are normally required.

EXAMPLE 4

1-(4-pyridinyl)-2-butanone 19.8 g of propionyl chloride dissolved in 20 ml of dichloromethane was added dropwise over 1 hour to 10 gm of 4-methylpyridine dissolved in 50 ml dichloromethane and maintained below 10° C. After addition, the reaction was brought to ambient temperature, stirred for 8 hours, then brought to reflux for 1 hour. The reaction mixture was quenched into saturated sodium carbonate solution, the organic layer separated and the solvent removed under reduced pressure. The residual 4-methylpyridine was removed by azeotropic distillation under reduced pressure with toluene. Ethanol was added and the mixture refluxed for 6 hours. The solvent was removed under reduced pressure to give 4.45 g of good (4-pyridinylmethyl) ethyl ketone.

EXAMPLE 5

2-(4-pyridinyl)-1-phenylethanone 30.2 g of benzoyl chloride dissolved in 30 cc of dichloromethane was added dropwise over 1 hour to 10 g of 4-methylpyridine dissolved in 60 cc dichloromethane and maintained at 10° C. during the addition. The reaction was brought to room temperature and stirred 16 hours. The reaction was brought to reflux for 1 hour, then cooled and quenched into saturated sodium carbonate solution. The organic layer was separated, solvent removed under reduced pressure and alcohol added. The mixture was refluxed 16 hours, then the solvent removed under reduced pressure. The residue was taken up in dichloromethane and washed two times with 3N HCl. The organic layer was separated and the aqueous acid layer first neutralized, then saturated with sodium carbonate. Dichloromethane extraction of the product, solvent removal and azeotropic removal of excess unreacted 4-methylpyridine using toluene gave 4.85 g of desired product.

We claim:

1. A process for preparing a compound of formula II

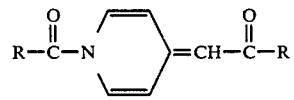

or acid addition salts thereof wherein R represents $C_1$–$C_5$ alkyl or phenyl which comprises reacting an acylating agent selected from an acyl halide of formula R-CO-X, an anhydride of formula R-CO-O-CO-R and mixtures thereof wherein R is as defined above and X is halogen, with 4-methylpyridine, in solution in a suitable solvent under substantially anhydrous conditions, and using a molar ratio of acylating agent to 4-methylpyridine of from about 5:1 to 1:1, with or without a strong anhydrous acid catalyst.

2. The process of claim 1 wherein X is selected from chlorine and bromine.

3. The process of claim 1 wherein said molar ratio is from about 2.1:1 to about 1.5:1.

4. The process of claim 3 wherein the acylating agent is an acyl halide of formula

wherein R is selected from methyl, ethyl and phenyl.

5. The process of claim 3 wherein the acylating agent is acetyl chloride.

6. The process of claim 1 wherein the acylating agent is acyl anhydride and the reaction is acid catalyzed with a strong anhydrous acid selected from HCl, HBr, HI, $H_2SO_4$, p-toluenesulfonic acid, methanesulfonic acid and trifluoroacetic acid.

7. The process of claim 6 wherein said acid is selected from HCl and $H_2SO_4$.

* * * * *